United States Patent
Koo et al.

(10) Patent No.: US 8,895,319 B2
(45) Date of Patent: Nov. 25, 2014

(54) NANOHYBRID NITROGEN MONOXIDE DETECTING SENSOR AND A PRODUCTION METHOD THEREFOR

(75) Inventors: Eunhae Koo, Daejeon (KR); Sung-ho Yoon, Seoul (KR); Jong-chul Lee, Seoul (KR); Jong-hee Kim, Seoul (KR)

(73) Assignee: Korea Institute of Ceramic Engineering and Technology, Seoul (KR)

( * ) Notice: Subject to any disclaimer, the term of this patent is extended or adjusted under 35 U.S.C. 154(b) by 286 days.

(21) Appl. No.: 13/265,095

(22) PCT Filed: Mar. 16, 2010

(86) PCT No.: PCT/KR2010/001630
§ 371 (c)(1),
(2), (4) Date: Oct. 18, 2011

(87) PCT Pub. No.: WO2011/074742
PCT Pub. Date: Jun. 23, 2011

(65) Prior Publication Data
US 2012/0244626 A1 Sep. 27, 2012

(30) Foreign Application Priority Data
Dec. 17, 2009 (KR) ......... 10-2009-0126140

(51) Int. Cl.
*G01N 21/64* (2006.01)
*G01N 21/00* (2006.01)
*B82Y 15/00* (2011.01)
*G01N 33/18* (2006.01)

(52) U.S. Cl.
CPC ........ *G01N 21/6489* (2013.01); *G01N 33/1826* (2013.01); *G01N 2021/6432* (2013.01); *G01N 33/18* (2013.01); *Y10S 977/774* (2013.01); *Y10S 977/773* (2013.01); *Y10S 977/70* (2013.01)
USPC ........... 436/116; 436/106; 977/774; 977/773; 977/700

(58) Field of Classification Search
CPC ......... G01N 21/64; G01N 21/00; B82Y 15/00
USPC ................... 436/116, 106; 977/774, 773, 700
See application file for complete search history.

(56) References Cited

FOREIGN PATENT DOCUMENTS

KR 10-2008-0074548 A 8/2008
KR 10-0858765 B1 9/2008

OTHER PUBLICATIONS

Yong Tae Kim et al, A multi-color method of semiconductor quantum-dots form single source semiconductors by oxidation in the solution. KR 10-0858765. Machine Translation obtained on May 28, 2014.*

(Continued)

*Primary Examiner* — Christine T Mui
(74) *Attorney, Agent, or Firm* — Levenfeld Pearlstein, LLC

(57) ABSTRACT

The present invention provides a nanohybrid type nitrogen monoxide detecting sensor and a production method therefor in which the nanohybrid type nitrogen monoxide detecting sensor includes a fluorescent semiconducting quantum dot and a transition metal compound. Employing a nanohybrid structure including semiconducting quantum dot nano-particles combined with a molecule recognizer selectively forming a bonding to nitrogen monoxide, the nitrogen monoxide detecting sensor is enabled to detect an infinitesimal amount of nitrogen monoxide by bringing about photoluminescence upon detection of nitrogen monoxide.

8 Claims, 1 Drawing Sheet

(56) References Cited

OTHER PUBLICATIONS

Neuman et al. "Quantum Dot Fluorescence Quenching Pthways with Cr (III) Complexes. Photosensitized NO Production from trans-Cr (cyclaim) (ONO)+" In NH-PA Author manuscript J Am Chem Soc.: available in PMC Apr. 13, 2009 See pp. 2-4.

International Search Report for PCT/KR2010/001630, dated Dec. 30, 2010.

* cited by examiner

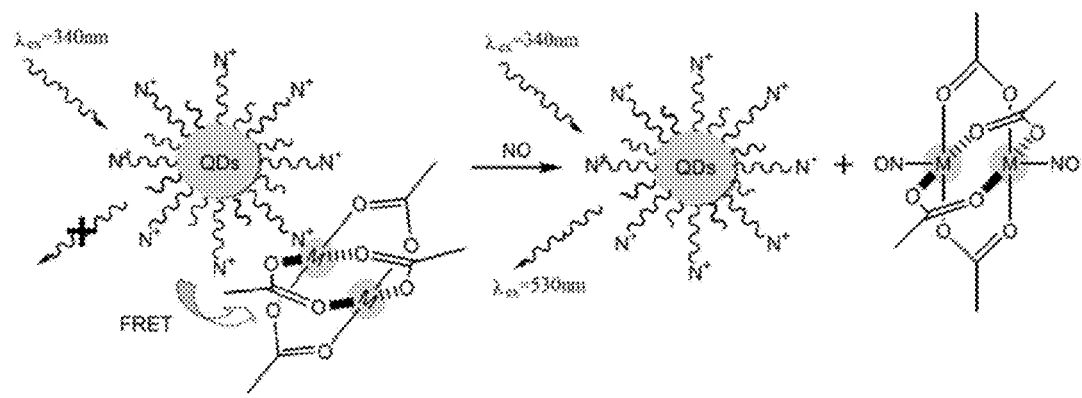

NANOHYBRID NITROGEN MONOXIDE DETECTING SENSOR AND A PRODUCTION METHOD THEREFOR

CROSS-REFERENCE TO RELATED APPLICATIONS

This is a National Stage Application of International Patent Application No. PCT/KR2010/001630, filed Mar. 16, 2010, which claims the benefit of and priority to Korean Patent Application No. 10-2009-0126140, filed Dec. 17, 2009, the contents of each of which are incorporated fully by reference herein.

TECHNICAL FIELD

The present invention relates to a nanohybrid type nitrogen monoxide detecting sensor and a production method therefor, and more particularly, to a nanohybrid type nitrogen monoxide detecting sensor which includes a fluorescent semiconducting quantum dot and a transition metal compound and a production method therefor.

BACKGROUND ART

Although considered as an air pollutant, nitrogen monoxide (NO) was reported to be a physiological active substance that plays a very important role in promoting vasodilation and blood circulation in the humane cardiovascular system. Prof. Louis Ignarro was awarded the 1998 Nobel Prize for his work to demonstrate the discovery. Since then, it has been revealed that nitrogen monoxide has a connection to various physiological phenomena and diseases in the neurotransmission system which controls learning, memory and pain alleviation, and the cardiovascular and immune systems.

As well known, the nitrogen monoxide (NO) production in human body takes place as three types of nitrogen monoxide synthases convert L-arginine to L-citrulline. Nitrogen monoxide (NO), which is produced at level of several nanomoles in the cardiovascular and nervous systems and at level of several micromoles in macrophages playing an important role in relation to the immune system, eliminates the infecting bacteria or viruses in human body.

Determining the production time, amount and distribution of nitrogen monoxide production in human body gives decisive clues to the numerous physiological mechanisms in which nitrogen monoxide participates, and thus many institutions have been studying on the measurement of nitrogen monoxide. However, the accurate concentration of nitrogen monoxide is hard to determine because nitrogen monoxide molecules are such a tiny substance about 30 dalton in molecular weight and reactive radicals which can freely diffuse through a cell membrane. The conventional methods for determining the concentration of nitrogen monoxide include an electrochemical method based on the oxidation-reduction reaction, a method of measuring photoluminescence pertaining to chemical reactions, or the like. Among these methods, the nitrogen monoxide measurement method using the electrochemical technique has been employed in many research institutions to determine the concentration of nitrogen monoxides. However, the measurement result in regard to the amount of nitrogen monoxide in a same portion of human body varies ranging from several hundred nanomoles to several dozens of micromoles, depending on the research institutions. This problem regarding selectivity occurs because different kinds of physiological active substances, such as dopamine, tyrosine, 5-hydroxytriptamine (5-HT), or the like, participate in the oxidation-reduction reactions in human body. To solve this problem, a polymer such as nafion is applied onto the outer surface of electrodes to enhance the selectivity to nitrogen monoxide. However, the thickness and the number of the polymer coatings may significantly affect the measurement results. On the other hand, the method of measuring photoluminescence pertaining to chemical reactions is the most success as a method commercially available to measure nitrogen monoxide, with a limitation as an indirect measurement method closely affected by the production amount of $N_2O_3$, reaction conditions, or the like. Instead of measuring nitrogen monoxide produced in human body, the method is to measure the amount of fluorescent dye produced when a nitrogen compound ($N_2O_3$) formed from nitrogen monoxide and oxygen reacts with the reaction precursor of an organic dye. Thus there is a demand for developing a sensor to accurately determine an infinitesimal concentration of nitrogen monoxide.

According to the research results obtained by the inventors of the present invention, it is possible to detect an infinitesimal amount of nitrogen monoxide by using a nanohybrid structure that includes semiconducting quantum dot nanoparticles combined with a molecule recognizer selectively forming a bonding to nitrogen monoxide, thereby completing the present invention.

DISCLOSURE

Technical Problem

Accordingly, it is an object of the present invention to provide a nanohybrid type nitrogen monoxide detecting sensor capable of selectively detecting an infinitesimal amount of nitrogen monoxide at the level of several nanomoles or less.

It is another object of the present invention to provide a method for producing the nanohybrid nitrogen monoxide detecting sensor.

Technical Solution

To achieve the above objects, the present invention provides a nanohybrid type nitrogen monoxide detecting sensor including: a fluorescent semiconducting quantum dot; and a transition metal compound.

The semiconducting quantum dot is at least one compound selected from the group consisting of a Group 12-16 semiconducting compound; a Group 13-15 semiconducting compound; and a Group 14 semiconducting compound, preferably a Group 12-16 semiconducting compound.

The semiconducting quantum dot is of a core-shell structure. The material constituting the core structure is at least one compound selected from the group consisting of a Group 12-16 semiconducting compound; a Group 13-15 semiconducting compound; and a Group 14 semiconducting compound, with an average particle diameter of 2 to 7 nm. On the other hand, the shell structure is a one-to-ten-layered ZnS single molecule layer.

The semiconducting quantum dot is surface-modified to have at least one functional group selected from the group consisting of amine, amine salt, and carboxyl.

The transition metal compound includes at least one transition metal selected from the group consisting of iron (Fe), cobalt (Co), copper (Cu), ruthenium (Ru) and rhodium (Rh).

The ligand constituting the transition metal compound is at least one selected from the group consisting of carboxyl, amine, porphyrin and thiol.

The present invention also provides a method for producing a nanohybrid type nitrogen monoxide detecting sensor that includes: acquiring semiconducting quantum dot particles; surface-modifying the quantum dot particles; and causing the surface-modified quantum dot particles to react/ mix with a transition metal compound.

Advantageous Effects

The nanohybrid type nitrogen monoxide detecting sensor of the present invention emits light from blue to red depending on the composition and size of the quantum dot upon detection nitrogen monoxide, thereby detecting an infinitesimal amount of nitrogen monoxide at a level of several nanomoles or less, and selectively detecting nitrogen monoxide without interference of other nitrogen oxide compounds.

DESCRIPTION OF DRAWINGS

FIG. 1 is a schematic view showing the detection principle of the nanohybrid type nitrogen monoxide detecting sensor of the present invention.

MODE FOR INVENTION

The nanohybrid type nitrogen monoxide detecting sensor of the present invention includes: a fluorescent semiconducting quantum dot; and a transition metal compound.

The semiconducting quantum dot is at least one compound selected from the group consisting of a Group 12-16 semiconducting compound; a Group 13-15 semiconducting compound; and a Group 14 semiconducting compound. The examples of the Group 12-16 semiconducting compound include ZnS, ZnSe, CdS, CdSe, CdTe, HgS, HgSe, or their mixtures. The examples of the Group 13-15 semiconducting compound include GaAs, InGaAs, InP, InAs, or their mixtures, and those of the Group 14 semiconducting compound include Ge, Si, or the like.

Preferably, the semiconducting quantum dot has a core-shell structure, which is designed to store the semiconducting nanoparticle, or to prevent a reduction or the fluorescent characteristic of semiconducting nano-particles caused by light exposure. The material constituting the core structure is at least one compound selected from the group consisting of a Group 12-16 semiconducting compound; a Group 13-15 semiconducting compound; and a Group 14 semiconducting compound. The shell structure is a one-to-ten-layered ZnS single molecule layer formed on the core structure.

To measure the nitrogen monoxide concentration in human body, the semiconducting quantum dot is required to be diffusible in the aqueous phase and thus preferably surface-modified to have amine, amine salt, or carboxyl groups on the surface. For this purpose, there may be used hexadecyl trimethyl ammonium bromide (CTAB), cysteine, thiol acid, amino propyl trimetoxy silane, and so forth.

The transition metal compound may include at least one transition metal selected from the group consisting of iron (Fe), cobalt (Co), copper (Cu), ruthenium (Ru) and rhodium (Rh). The ligand constituting the transition metal compound may include at least one selected from the group consisting of carboxyl, amine, porphyrin and thiol.

The method for producing a nanohybrid type nitrogen monoxide detecting sensor according to the present invention includes: decomposing an organometallic compound precursor through pyrolysis to synthesize a quantum dot having a core-shell structure; surface-modifying the quantum dot to synthesize an aqueous quantum dot; and causing the aqueous quantum dot to react with a transition metal compound.

At first, the quantum dot constituting the core of the core-shell structure is synthesized using a commonly well-known organometallic compound as a precursor through pyrolysis. To form a shell structure, the ZnS solution is slowly added dropwise with a syringe pump and then stirred at 150 to 250° C. for about 1 to 1.5 hour.

Subsequently, the quantum dot thus synthesized is dispersed in an organic solvent such as chloroform ($CHCl_3$) or the like. The resultant quantum dot solution is mixed with a solution of surface modifying agent (such as hexadecyl trimethyl ammonium bromide (CTAB), etc) and then stirred for a defined period of time to achieve surface modification.

Finally, the aqueous solution of the surface-modified quantum dot particles is mixed with 1 to 100 equivalent weight of a transition metal compound per one equivalent weight of the quantum dot, and the mixture is stirred at the room temperature for over 7 hours to manufacture a nanohybrid sensor for detecting nitrogen monoxide.

Hereinafter, the function of the nanohybrid type nitrogen monoxide detecting sensor of the present invention will be described with reference to FIG. 1. FIG. 1 is a schematic view showing the detection principle of the nanohybrid type nitrogen monoxide detecting sensor of the present invention.

Referring to FIG. 1, without nitrogen monoxide (left side to the arrow), light irradiation is imposed on a solution in which the nanohybrid type nitrogen monoxide detecting sensor of the present invention is dispersed, to excite one electron from the valence band in the quantum dot of the detecting sensor to the conduction band. Meanwhile, the hole of the valence band is immediately filled with an electron in the d-orbital of the transition metal, and the excited electron of the conduction band transfers to the d-orbital of the transition metal, thereby quenching the photoluminescence of the quantum dot and emitting heat to stop emission of light. Otherwise, when there exists nitrogen monoxide (right side to the arrow), the nitrogen monoxide radical that is highly reactive as a ligand combines with the transition metal to form a complex compound, leaving from the quantum dot. This causes the sensor to emit light in the presence of nitrogen monoxide. In this case, the transition metal is far distant from the quantum dot, so the quenching of photoluminescence disappears. This phenomenon is very similar to the mechanism of the turn-on fluorescent sensor based on the so-called PET (Photoinduced Electron Transfer) mechanism. In other words, the detecting sensor functions as a high sensitive and selective nitrogen monoxide sensor which is designed to emit light in the presence of nitrogen monoxide but not to cause photoluminescence in absence of nitrogen monoxide.

Upon detection of nitrogen monoxide, the detecting sensor emits light from blue to red, depending on the composition and size of the quantum dot, to show whether nitrogen monoxide exists or not. As the photoluminescence becomes stronger with an increase in the amount of nitrogen monoxide, the nitrogen monoxide concentration can be determined based on the strength of the photoluminescence.

While the invention will be described in connection with specific and preferred examples, it will be understood that it is not intended to limit the invention to those embodiments. To the contrary, it is intended to cover all alterations, modifications and equivalents as may be included within the spirit and scope of the invention as defined by the appended claims.

Example 1

1. Preparation of Nanohybrid Type Sensor

First, a CdSe/ZnS quantum dot having a core-shell structure was acquired. The CdSe quantum dot constituting the quantum dot core was synthesized from an organometallic precursor, cadmium oxide (CdO) and selenium powder through pyrolysis at a reaction temperature of 300 to 320° C. A ZnS solution prepared by dissolving zinc stearate and sulfur (S) powder in tri-n-butylphosphine was slowly added at a flow of 0.1 ml/min using a syringe pump and then stirred at 190° C. for about 1.5 hour to synthesize a CdSe/ZnS core-shell quantum dot.

Subsequently, the quantum dot thus synthesized was dispersed in organic solvent, chloroform ($CHCl_3$). To synthesize an aqueous quantum dot solution, the resultant quantum dot solution was mixed with a solution of hexadecyl trimethyl ammonium bromide (CTAB) and then stirred for a defined period of time to achieve surface modification with CTAB.

Finally, the aqueous solution of the surface-modified quantum dot particles was mixed with 10 equivalent weight of rhodium acetate as a transition metal compound per one equivalent weight of the quantum dot. The mixture was stirred at the room temperature for 7 hours to prepare a nanohybrid type sensor for detecting nitrogen monoxide.

2. Measurement of Sensitivity to Nitrogen Monoxide

To measure the sensitivity characteristic of the nitrogen monoxide detecting sensor, a defined amount of diethylamine sodium salt hydrate (NO/NOate) capable of producing nitrogen monoxide based on the quantum dot concentration was mixed with the quantum dot hybrid solution to cause a reaction, and the photoluminescence strength was measured using a PL spectrometer (Science, S-3100). If there was a difference in the measured photoluminescence strength before and after the reaction, the least concentration of diethylamine sodium salt hydrate was defined as the sensitivity to nitrogen monoxide.

As determined according to the above-described measurement method, the sensitivity of the nanohybrid sensor of Example 1 to nitrogen monoxide was 5 nanomoles.

Example 2

To prepare a nanohybrid sensor and measure the sensitivity of the sensor to nitrogen monoxide, the procedures were performed in the same manner as described in Example 1, excepting that InP/ZnS quantum dot was used instead of CdSe/ZnS. The sensitivity of the nanohybrid sensor to nitrogen monoxide was 10 nanomoles.

Example 3

To prepare a nanohybrid sensor and measure the sensitivity of the sensor to nitrogen monoxide, the procedures were performed in the same manner as described in Example 1, excepting that the quantum dot was modified with cystein instead of CTAB used to prepare the aqueous quantum dot. The sensitivity of the nanohybrid sensor to nitrogen monoxide was 10 nanomoles.

Example 4

To prepare a nanohybrid sensor and measure the sensitivity of the sensor to nitrogen monoxide, the procedures were performed in the same manner as described in Example 1, excepting that the quantum dot was modified with aminopropyl trimethoxy silane instead of CTAB used to prepare the aqueous quantum dot. The sensitivity of the nanohybrid sensor to nitrogen monoxide was 10 nanomoles.

Example 5

To prepare a nanohybrid sensor and measure the sensitivity of the sensor to nitrogen monoxide, the procedures were performed in the same manner as described in Example 2, excepting that the quantum dot was modified with cystein instead of CTAB used to prepare the aqueous quantum dot. The sensitivity of the nanohybrid sensor to nitrogen monoxide was 10 nanomoles.

Example 6

To prepare a nanohybrid sensor and measure the sensitivity of the sensor to nitrogen monoxide, the procedures were performed in the same manner as described in Example 1, excepting that copper acetate ($Cu(II)(OAc)_2$) was used instead of rhodium acetate as a transition metal compound. The sensitivity of the nanohybrid sensor to nitrogen monoxide was 60 nanomoles.

INDUSTRIAL APPLICABILITY

The nitrogen monoxide sensor of the present invention can be used to analyze the functions of nitrogen monoxide in the mechanism for accelerating blood circulation in human capillary vessels or transferring messages among neurons, and also in a variety of diseases such as cancer, diabetics, or senile disorders.

The invention claimed is:

1. A nanohybrid type nitrogen monoxide detecting sensor comprising:
    a fluorescent semiconducting quantum dot; and
    a transition metal compound, wherein the transition metal compound includes at least one transition metal selected from the group consisting of iron (Fe), cobalt (Co), copper (Cu), ruthenium (Ru) and rhodium (Rh), and a ligand selected from the group consisting of carboxyl, amine, porphyrin and thiol;
    wherein the fluorescent semiconducting quantum dot and the transition metal compound are bonded together to form the nanohybrid type nitrogen monoxide detecting sensor;
    wherein the nitrogen monoxide detecting sensor releases the fluorescent semiconducting quantum dot in presence of nitrogen monoxide, wherein the nitrogen monoxide detecting sensor signals detection of nitrogen monoxide by fluorescence of the fluorescent semiconducting quantum dot released from the nitrogen monoxide detecting sensor.

2. The nanohybrid type nitrogen monoxide detecting sensor as claimed in claim 1, wherein the fluorescent semiconducting quantum dot is at least one compound selected from the group consisting of a Group 12-16 semiconducting compound; a Group 13-15 semiconducting compound; and a Group 14 semiconducting compound.

3. The nanohybrid type nitrogen monoxide detecting sensor as claimed in claim 1, wherein the semiconducting quantum dot is of a core-shell structure.

4. The nanohybrid type nitrogen monoxide detecting sensor as claimed in claim 3, wherein a material constituting the core structure is at least one compound selected from the group consisting of a Group 12-16 semiconducting compound; a Group 13-15 semiconducting compound; and a Group 14 semiconducting compound.

5. The nanohybrid type nitrogen monoxide detecting sensor as claimed in claim 3, wherein the core structure has an average particle diameter of 2 to 7 nm.

6. The nanohybrid type nitrogen monoxide detecting sensor as claimed in claim 3, wherein the shell structure is a one-to-ten-layered ZnS single molecule layer.

7. The nanohybrid type nitrogen monoxide detecting sensor as claimed in claim 1, wherein the semiconducting quantum dot is surface-modified to have at least one functional group present on the surface thereof, the functional group being selected from the group consisting of amine, amine salt, and carboxyl.

8. A method for producing a nanohybrid type nitrogen monoxide detecting sensor, comprising:
- decomposing an organometallic compound precursor through pyrolysis to synthesize a quantum dot solution having a core-shell structure;
- surface-modifying the quantum dot solution to synthesize an aqueous quantum dot;
- causing the aqueous quantum dot to react with a transition metal compound to form a nanohybrid structure; and
- using the nanohybrid structure to detect nitrogen monoxide, wherein the nanohybrid structure emits light in presence of nitrogen monoxide.

* * * * *

UNITED STATES PATENT AND TRADEMARK OFFICE
CERTIFICATE OF CORRECTION

PATENT NO. : 8,895,319 B2
APPLICATION NO. : 13/265095
DATED : November 25, 2014
INVENTOR(S) : Koo et al.

It is certified that error appears in the above-identified patent and that said Letters Patent is hereby corrected as shown below:

Title Page, References Cited

On Page 2, under "OTHER PUBLICATIONS", column 1, line 1, "Pthways" to read as --Pathways--.

In the Specification

Column 1, line 67, "hydroxytriptamine" to read as --hydroxytryptamine--.

Column 3, line 56, "trimetoxy" to read as --trimethoxy--.

Column 5, line 56, "cystein" to read as --cysteine--.

Column 6, line 9, "cystein" to read as --cysteine--.

Signed and Sealed this
Fourteenth Day of April, 2015

Michelle K. Lee
*Director of the United States Patent and Trademark Office*